US012318273B2

(12) United States Patent
Zink et al.

(10) Patent No.: US 12,318,273 B2
(45) Date of Patent: *Jun. 3, 2025

(54) ABSORBENT ARTICLE WITH ABSORBENT CORE

(71) Applicant: The Procter & Gamble Company, Cincinnati, OH (US)

(72) Inventors: Ronald Joseph Zink, Blue Ash, OH (US); Masaharu Nishikawa, Cincinnati, OH (US); Gary Dean Lavon, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/192,718

(22) Filed: Mar. 30, 2023

(65) Prior Publication Data

US 2023/0293360 A1    Sep. 21, 2023

Related U.S. Application Data

(63) Continuation of application No. 17/078,120, filed on Oct. 23, 2020, now Pat. No. 11,648,159, which is a
(Continued)

(51) Int. Cl.
*A61F 13/15* (2006.01)
*A61F 13/49* (2006.01)
(Continued)

(52) U.S. Cl.
CPC ...... *A61F 13/496* (2013.01); *A61F 13/15203* (2013.01); *A61F 13/49011* (2013.01);
(Continued)

(58) Field of Classification Search
CPC .............. A61F 13/496; A61F 13/15203; A61F 13/49011; A61F 13/4906; A61F 13/495;
(Continued)

(56) References Cited

U.S. PATENT DOCUMENTS

| 3,848,594 A | 11/1974 | Buell |
| 3,860,003 A | 1/1975 | Buell |

(Continued)

FOREIGN PATENT DOCUMENTS

| EP | 1880700 A1 | 1/2008 |
| EP | 2241299 A1 | 10/2010 |

(Continued)

OTHER PUBLICATIONS

14614 PCT Search Report for PCT/US2017/066289 dated Feb. 15, 2018, 11 pages.

(Continued)

*Primary Examiner* — Jacqueline F Stephens
(74) *Attorney, Agent, or Firm* — Daniel S. Albrecht; Sarah DeCristofaro

(57) ABSTRACT

An absorbent article includes a first waist region, a second waist region, and a crotch region disposed between the first and second waist regions; and a chassis having a topsheet, a backsheet and an absorbent core. The article also includes a waist feature having a portion extending longitudinally outboard of the chassis in the waist region. The backsheet includes a barrier layer having a maximum length, $L_{BS}$. The absorbent core has absorbent material and a maximum length, $L_{CW}$. $L_{CW}$ is substantially the same as $L_{BS}$. The absorbent material is disposed in an absorbent material deposition area. The absorbent material deposition area has a maximum length, $L_{AB}$, and $L_{AB}$ is about 90% or greater of $L_{BS}$. The first absorbent area lateral edge is disposed a longitudinal distance, D1, from the first barrier lateral edge, and D1 is about 5% or less of $L_{BS}$.

20 Claims, 8 Drawing Sheets

Related U.S. Application Data continuation of application No. 15/841,352, filed on Dec. 14, 2017, now Pat. No. 10,898,393.

(60) Provisional application No. 62/436,045, filed on Dec. 19, 2016.

(51) Int. Cl.
| | | |
|---|---|---|
| *A61F 13/495* | (2006.01) | |
| *A61F 13/496* | (2006.01) | |
| *A61F 13/512* | (2006.01) | |
| *A61F 13/534* | (2006.01) | |
| *A61F 13/64* | (2006.01) | |
| *A61F 13/53* | (2006.01) | |

(52) U.S. Cl.
CPC ........ *A61F 13/4906* (2013.01); *A61F 13/495* (2013.01); *A61F 13/4963* (2013.01); *A61F 13/512* (2013.01); *A61F 13/534* (2013.01); *A61F 13/64* (2013.01); *A61F 2013/15406* (2013.01); *A61F 2013/15463* (2013.01); *A61F 2013/15552* (2013.01); *A61F 2013/49093* (2013.01); *A61F 2013/4953* (2013.01); *A61F 2013/530481* (2013.01); *A61F 2013/5349* (2013.01)

(58) Field of Classification Search
CPC .. A61F 13/4963; A61F 13/512; A61F 13/534; A61F 13/64; A61F 2013/15406; A61F 2013/15463; A61F 2013/15552; A61F 2013/49093; A61F 2013/4953; A61F 2013/530481; A61F 2013/5349
See application file for complete search history.

(56) References Cited

U.S. PATENT DOCUMENTS

| | | |
|---|---|---|
| 4,116,892 A | 9/1978 | Schwarz |
| 4,340,706 A | 7/1982 | Obayashi et al. |
| 4,610,678 A | 9/1986 | Weisman |
| 4,662,875 A | 5/1987 | Hirotsu |
| 4,673,402 A | 6/1987 | VVeisman et al. |
| 4,695,278 A * | 9/1987 | Lawson ............ A61F 13/49426 604/385.27 |
| 4,699,622 A | 10/1987 | Toussant |
| 4,834,735 A | 5/1989 | Alemany |
| 4,834,741 A | 5/1989 | Sabee |
| 4,846,815 A | 7/1989 | Scripps |
| 4,854,984 A | 8/1989 | Ball |
| 4,888,231 A | 12/1989 | Angstadt |
| 4,892,536 A | 1/1990 | Desmarais |
| 4,894,060 A | 1/1990 | Nestegard |
| 4,919,738 A | 4/1990 | Ball et al. |
| 4,946,527 A | 8/1990 | Battrell |
| 4,963,140 A | 10/1990 | Robertson |
| 4,990,147 A | 2/1991 | Freeland |
| 5,037,416 A | 8/1991 | Allen |
| 5,137,537 A | 8/1992 | Herron |
| 5,143,679 A | 9/1992 | Weber |
| 5,147,345 A | 9/1992 | Lavon |
| 5,151,092 A | 9/1992 | Buell |
| 5,156,793 A | 10/1992 | Buell |
| 5,167,897 A | 12/1992 | Weber |
| 5,221,274 A | 6/1993 | Buell |
| 5,242,436 A | 9/1993 | Weil |
| 5,260,345 A | 11/1993 | Desmarais |
| 5,266,392 A | 11/1993 | Land |
| 5,269,775 A | 12/1993 | Freeland |
| 5,340,648 A | 8/1994 | Rollins et al. |
| 5,342,338 A | 8/1994 | Roe |
| 5,382,400 A | 1/1995 | Pike et al. |
| 5,387,207 A | 2/1995 | Dyer |
| 5,397,316 A | 3/1995 | Young |
| 5,418,045 A | 5/1995 | Pike et al. |
| 5,422,172 A | 6/1995 | Wu |
| 5,499,978 A | 3/1996 | Buell |
| 5,501,756 A | 3/1996 | Rollins et al. |
| 5,507,736 A | 4/1996 | Clear |
| 5,507,909 A | 4/1996 | Rollins et al. |
| 5,518,801 A | 5/1996 | Chappell |
| 5,554,145 A | 9/1996 | Roe |
| 5,569,234 A | 10/1996 | Buell |
| 5,571,096 A | 11/1996 | Dobrin |
| 5,580,411 A | 12/1996 | Nease |
| 5,591,152 A | 1/1997 | Buell |
| 5,607,760 A | 3/1997 | Roe |
| 5,609,587 A | 3/1997 | Roe |
| 5,625,222 A | 4/1997 | Yoneda |
| 5,635,191 A | 6/1997 | Roe |
| 5,643,588 A | 7/1997 | Roe |
| 5,707,468 A | 1/1998 | Arnold et al. |
| 5,849,816 A | 12/1998 | Suskind et al. |
| 5,865,823 A | 2/1999 | Curro |
| 5,989,236 A | 11/1999 | Roe et al. |
| 6,004,306 A | 12/1999 | Robles |
| 6,077,375 A | 6/2000 | Kwok |
| 6,107,537 A | 8/2000 | Elder |
| 6,120,487 A | 9/2000 | Ashton |
| 6,200,635 B1 | 3/2001 | Kwok |
| 6,235,137 B1 | 5/2001 | Van Eperen et al. |
| 6,258,076 B1 | 7/2001 | Glaug et al. |
| 6,315,764 B1 | 11/2001 | Faulks et al. |
| 6,361,634 B1 | 3/2002 | White et al. |
| 6,432,098 B1 | 8/2002 | Kline |
| 6,454,989 B1 | 9/2002 | Neely et al. |
| 6,506,185 B1 * | 1/2003 | Sauer ................ A61F 13/49466 604/385.101 |
| 6,520,237 B1 | 2/2003 | Bolyard, Jr. et al. |
| 6,561,430 B2 | 5/2003 | Ou |
| 6,582,518 B2 | 6/2003 | Riney |
| 6,610,161 B2 | 8/2003 | Erdman |
| 6,613,146 B2 | 9/2003 | Bolyard, Jr. |
| 6,632,386 B2 | 10/2003 | Shelley et al. |
| 6,645,569 B2 | 11/2003 | Cramer |
| 6,652,693 B2 | 11/2003 | Burriss et al. |
| 6,719,846 B2 | 4/2004 | Nakamura et al. |
| 6,737,102 B1 | 5/2004 | Saidman et al. |
| 6,863,933 B2 | 3/2005 | Cramer |
| 7,112,621 B2 | 9/2006 | Rohrbaugh |
| 7,291,239 B2 | 11/2007 | Polanco et al. |
| 7,435,243 B2 | 10/2008 | Miyamoto |
| 7,744,576 B2 | 6/2010 | Busam |
| 8,062,279 B2 | 11/2011 | Miyamoto |
| 8,728,051 B2 | 5/2014 | Lu |
| 8,939,957 B2 | 1/2015 | Raycheck |
| 9,301,889 B2 | 4/2016 | Miyamoto |
| 9,421,137 B2 | 8/2016 | Lavon |
| 10,898,393 B2 | 1/2021 | Zink et al. |
| 11,648,159 B2 * | 5/2023 | Zink ................ A61F 13/15203 604/385.24 |
| 2003/0148684 A1 | 8/2003 | Cramer et al. |
| 2004/0158212 A1 * | 8/2004 | Ponomarenko ....... A61F 13/534 604/367 |
| 2004/0181200 A1 | 9/2004 | Desai et al. |
| 2004/0193133 A1 | 9/2004 | Desai et al. |
| 2005/0008839 A1 | 1/2005 | Cramer |
| 2007/0078422 A1 | 4/2007 | Glaug et al. |
| 2009/0088718 A1 | 4/2009 | Toyoshima |
| 2009/0192035 A1 | 7/2009 | Stueven et al. |
| 2009/0258994 A1 | 10/2009 | Stueven et al. |
| 2010/0040826 A1 | 2/2010 | Mansfield et al. |
| 2010/0068520 A1 | 3/2010 | Stueven |
| 2011/0250413 A1 | 10/2011 | Lu |
| 2011/0268932 A1 | 11/2011 | Catalan |
| 2011/0319846 A1 | 12/2011 | Rinnert et al. |
| 2011/0319848 A1 | 12/2011 | Mckiernan |
| 2012/0316526 A1 | 12/2012 | Rosati et al. |
| 2013/0079742 A1 | 3/2013 | Kuwano et al. |
| 2014/0163503 A1 | 6/2014 | Arizti |
| 2014/0274642 A1 | 9/2014 | Lavon et al. |
| 2014/0276525 A1 | 9/2014 | Lavon et al. |

(56) References Cited

U.S. PATENT DOCUMENTS

| | | | |
|---|---|---|---|
| 2016/0030256 A1* | 2/2016 | Kreuzer | A61F 13/533 493/383 |
| 2016/0095764 A1 | 4/2016 | Seitz | |
| 2016/0270972 A1 | 9/2016 | Surushe et al. | |
| 2016/0331601 A1 | 11/2016 | Lavon et al. | |
| 2017/0056256 A1 | 3/2017 | Smith | |
| 2018/0168888 A1 | 6/2018 | Zink | |
| 2018/0369027 A1 | 12/2018 | Fukasawa et al. | |
| 2021/0085533 A1 | 3/2021 | Zink et al. | |

FOREIGN PATENT DOCUMENTS

| | | |
|---|---|---|
| EP | 2399557 B2 | 3/2017 |
| EP | 3360522 A1 | 8/2018 |
| JP | 2004329238 A | 11/2004 |
| JP | 2005074157 A | 3/2005 |
| JP | 2009207565 A | 9/2009 |
| WO | 9516746 A1 | 6/1995 |
| WO | 02069871 A1 | 9/2002 |
| WO | 2005110731 A2 | 11/2005 |
| WO | 2006004872 A2 | 1/2006 |
| WO | 2006083584 A2 | 8/2006 |
| WO | 2007046052 A1 | 4/2007 |
| WO | 2007047598 A1 | 4/2007 |
| WO | 2008155699 A1 | 12/2008 |
| WO | 2009155264 A1 | 12/2009 |
| WO | 2009155265 A1 | 12/2009 |
| WO | 2010051937 A1 | 5/2010 |
| WO | 2010109866 A1 | 9/2010 |
| WO | 2013029952 A1 | 3/2013 |
| WO | 2014093129 A1 | 6/2014 |
| WO | 2016029654 A1 | 3/2016 |
| WO | 2016029658 A1 | 3/2016 |
| WO | 2016033282 A1 | 3/2016 |
| WO | 2016054497 A1 | 4/2016 |
| WO | 2016057736 A1 | 4/2016 |
| WO | 2016174779 A1 | 11/2016 |
| WO | 2016175780 A1 | 11/2016 |
| WO | 2017061568 A1 | 4/2017 |
| WO | 2017169380 A1 | 10/2017 |

OTHER PUBLICATIONS

14614 Third Party Opposition for 17826055.0 dated Aug. 12, 2022, 22 pages.
14614 Third Party Opposition for 17826055.0 dated Aug. 16, 2022, 31 pages.
All Office Actions, U.S. Appl. No. 17/078,120; filed on Oct. 23, 2020.
All Office Actions; U.S. Appl. No. 15/841,352; filed on Dec. 14, 2017.
Wikipedia, "Urinary Bladder", The Wayback Machine—http://web.archive.org/web/20160809170657/https://en.wikipedia.org/wiki/urinary_bladder; dated Jul. 27, 2022, 5 Pages.

* cited by examiner

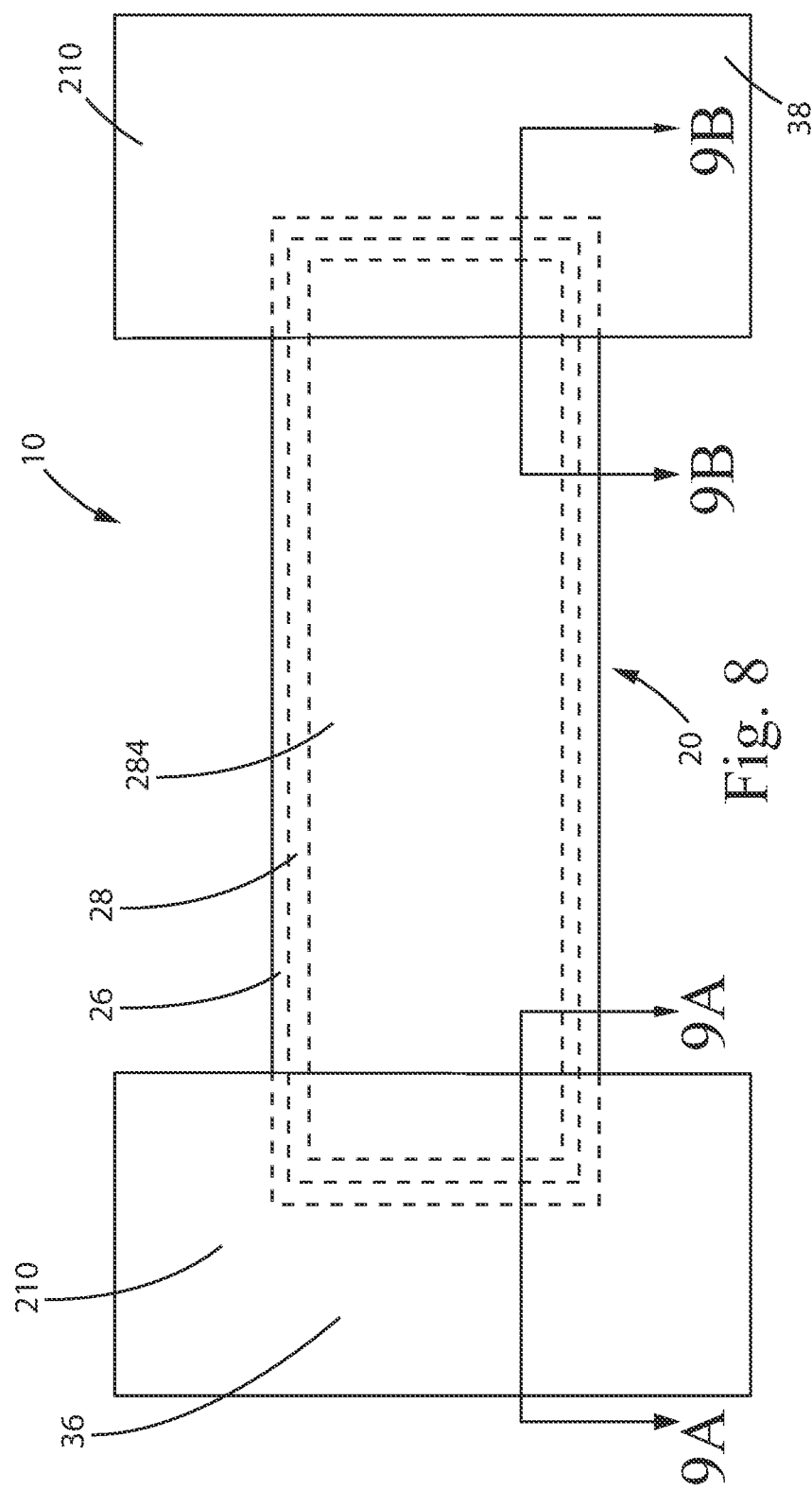

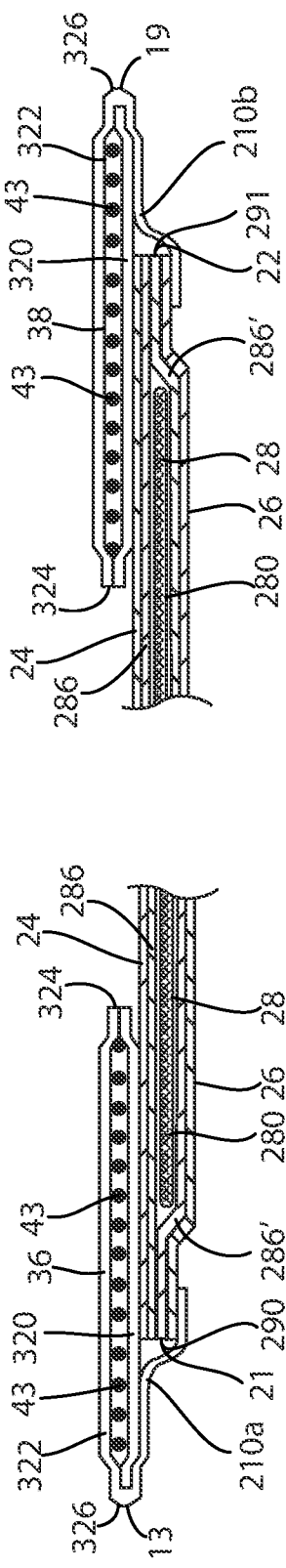

ABSORBENT ARTICLE WITH ABSORBENT CORE

CROSS REFERENCE TO RELATED APPLICATIONS

This application is a continuation of, and claims priority under 35 U.S.C. § 120 to, U.S. patent application Ser. No. 15/841,352, filed on Dec. 14, 2017, which claims the benefit, under 35 U.S.C. § 119(e), of U.S. Provisional Patent Application Ser. No. 62/436,045 filed on Dec. 19, 2016, the entire disclosures of which are fully incorporated by reference herein.

FIELD OF THE INVENTION

This invention relates to absorbent articles, in particular absorbent articles having absorbent cores. The articles may have improved functional and/or communicative properties.

BACKGROUND OF THE INVENTION

Disposable absorbent articles for receiving and retaining bodily discharges such as urine or feces are well known in the art. Examples of these include disposable diaper(s), training pants and adult incontinence articles. Typically, disposable diapers comprise a liquid pervious topsheet that faces the wearer's body, a liquid impervious backsheet that faces the wearer's clothing and an absorbent core interposed between the liquid pervious topsheet and the backsheet.

An important component of disposable absorbent articles is the absorbent core. The absorbent core typically includes superabsorbent polymer material, such as hydrogel-forming polymer material, also referred to as absorbent gelling material, AGM, or superabsorbent polymer, SAP. This superabsorbent polymer material ensures that large amounts of bodily fluids, e.g. urine, can be absorbed by the absorbent article during its use and be locked away, thus providing low rewet and good skin dryness.

However, given manufacturing constraints, manufacturers to date have struggled with maximizing the absorbent area of disposable articles. Indeed, absorbent cores must be fashioned and placed in a way that will not slow down the production line and/or cause undesired cutting of the core and/or improper positioning, or the like. For example, after cutting the individual absorbent cores from a continuous web of absorbent cores, each individual core may have to be precisely placed in desired positions on advancing topsheet or backsheet webs. In some manufacturing configurations, the speeds of the individual absorbent cores will need to be increased or decreased before placement on the topsheet or backsheet webs. In some instances, adhesives will also need to be applied in discrete zones on the advancing webs, requiring relatively frequent on/off cycling of adhesive applicators. To help ensure quality production, the individual absorbent core placement may need to be closely monitored and controlled with relatively high speed sensor and associated controller technologies. As such, the machinery required to precisely cut, place, control, and/or bond the individual cores to advancing webs may add complexities and expense to a manufacturing line while at the same time reducing reliability. In addition, the aforementioned challenges may be exacerbated in absorbent article assembly processes operating at relatively high speed production rates and/or configured to assemble relatively small sized absorbent articles. Addressing these issues in one type of product may require different parameters and controls than when addressing the same issues in another type of product.

Further, one way that manufacturers balance providing quality products with maintaining lower production costs is by using the same components in different types of articles. For instance, while training pants and taped diapers are constructed differently and have certain functional differences, a manufacturer may use the same absorbent core in both types of articles rather than creating a unique absorbent core for each type of article constructed. Indeed, creation of different base components results in more production costs (e.g., additional lines, machinery, production time, etc.). As such, manufacturers may use a component (e.g., an absorbent core) in more than one type of article by resizing, repositioning or otherwise altering the components (or portions of the article) for incorporation of the component into the various articles. However, such resizing, repositioning and/or altering results in increased complexities in manufacturing, such as additional processes steps.

Further still, in attempting to increase the absorbent footprint of absorbent articles, manufacturers have had to compromise other features. For instance, channels which may be void of absorbent material but enhance comfort and fit may be sacrificed for greater absorbency. Likewise, waist features and belts requiring a relatively large area to ensure proper fit may be reduced in size in order to increase space for absorbent material.

Because of the issues faced by manufacturers, absorbent articles often have inefficient use of space and therefore less absorbency than possible. Therefore, there is a need for an article that efficiently utilizes the available space. In addition, there is a need for an article that has desirable absorbency while also providing comfort and/or fit. There is also a need for an article with desired absorbency while visually assuring the product will perform as desired and providing a garment-like and/or soft appearance.

SUMMARY OF THE INVENTION

An absorbent article comprises a first waist region, a second waist region, and a crotch region disposed between the first and second waist regions; and a longitudinal centerline and a lateral centerline. The article further includes a chassis comprising a topsheet, a backsheet and an absorbent core disposed between the topsheet and the backsheet. The absorbent core may comprise absorbent material disposed in an absorbent material deposition area. A waist feature is joined to the chassis in the first and/or second waist region. The waist feature includes a free portion which extends longitudinally outboard of the chassis in said first and/or second region.

In certain embodiments, the backsheet comprises a barrier layer having a maximum length, $L_{BS}$, extending between a first barrier lateral edge and a second barrier lateral edge. The absorbent core comprises a core wrap enclosing the absorbent material and having a maximum length, $L_{CW}$. The absorbent material deposition area comprises a maximum length, $L_{AB}$, extending between a first absorbent area lateral edge and a second absorbent area lateral edge. $L_{CW}$ may be substantially the same as $L_{BS}$, and $L_{AB}$ may be about 90% or greater of $L_{BS}$. The first absorbent area lateral edge may be disposed a longitudinal distance, D1, from the first barrier lateral edge, wherein D1 is 5% or less of $L_{BS}$.

In further embodiments, the backsheet comprises a barrier layer having a maximum length, $L_{BS}$, extending between a first barrier lateral edge and a second barrier lateral edge; and the absorbent core comprises absorbent material disposed in an absorbent material deposition area having a first absorbent area lateral edge and a second absorbent area lateral edge. The first absorbent area lateral edge may be within about 50 mm of the first waist edge, and the free portion may comprise a length, E, of at least about 10 mm. The absorbent material may comprise about 15% or less by weight of cellulosic material.

In some embodiments, the backsheet comprises a barrier layer having a barrier layer area and the absorbent material deposition area comprises an absorbent area. The absorbent area may be at least about 90% of the barrier layer area.

BRIEF DESCRIPTION OF THE DRAWINGS

FIG. 8 is a schematic plan view of an exemplary absorbent pant precursor structure according to a nonlimiting embodiment of the present invention.

FIG. 9A is a schematic cross-sectional view of the absorbent pant of FIG. 8 taken along line 9A-9A.

FIG. 9B is a schematic cross-sectional view of the absorbent pant of FIG. 8 taken along line 9B-9B.

DETAILED DESCRIPTION OF THE INVENTION

Definitions

Figure 1:
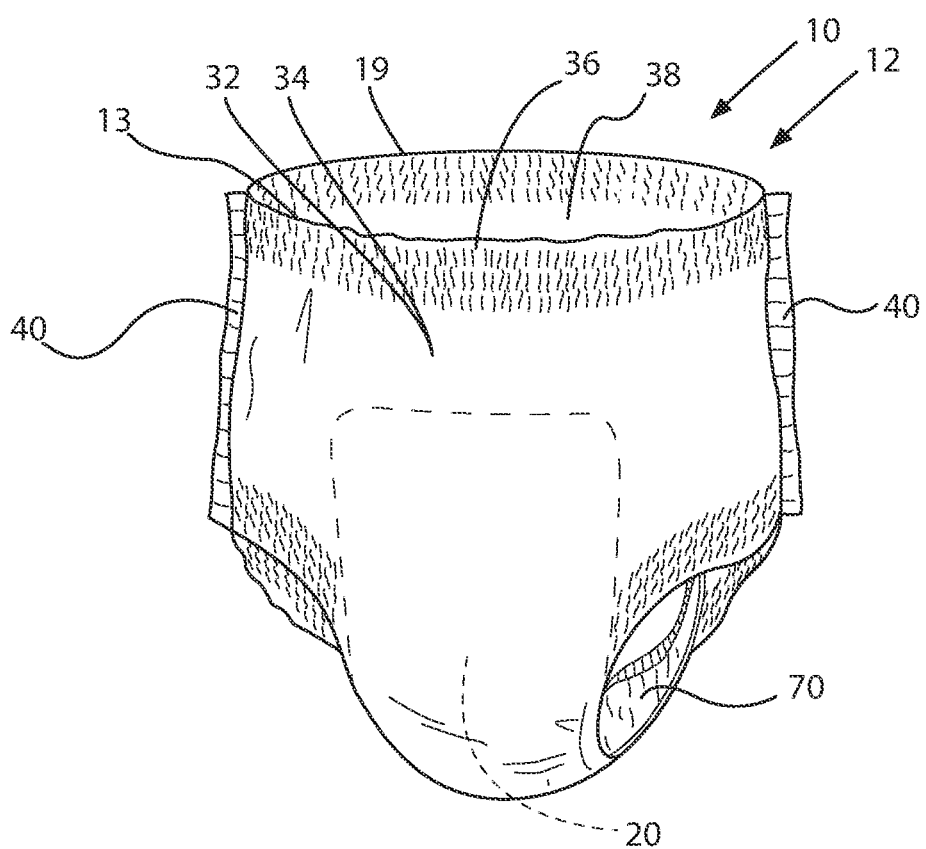
FIG. 1 is a perspective view of an exemplary absorbent pant according to one nonlimiting embodiment of the present invention.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like. In embodiments, absorbent articles may be disposable.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal."

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor (i.e., may be "vapor-permeable").

"Elongatable," "extensible," or "stretchable" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery). Elastomeric materials may include elastomeric films (including but not limited to films derived from rubber and/or other polymeric materials), polyurethane films, elastomeric foams, scrims, elastic nonwovens, synthetic fibers such as LYCRA© and other sheet-like structures.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

Absorbent Article

Although examples of the invention are described herein as in reference to a pant, other forms of absorbent articles (e.g., taped diapers) are within the scope of the invention as well.

Figure 2:
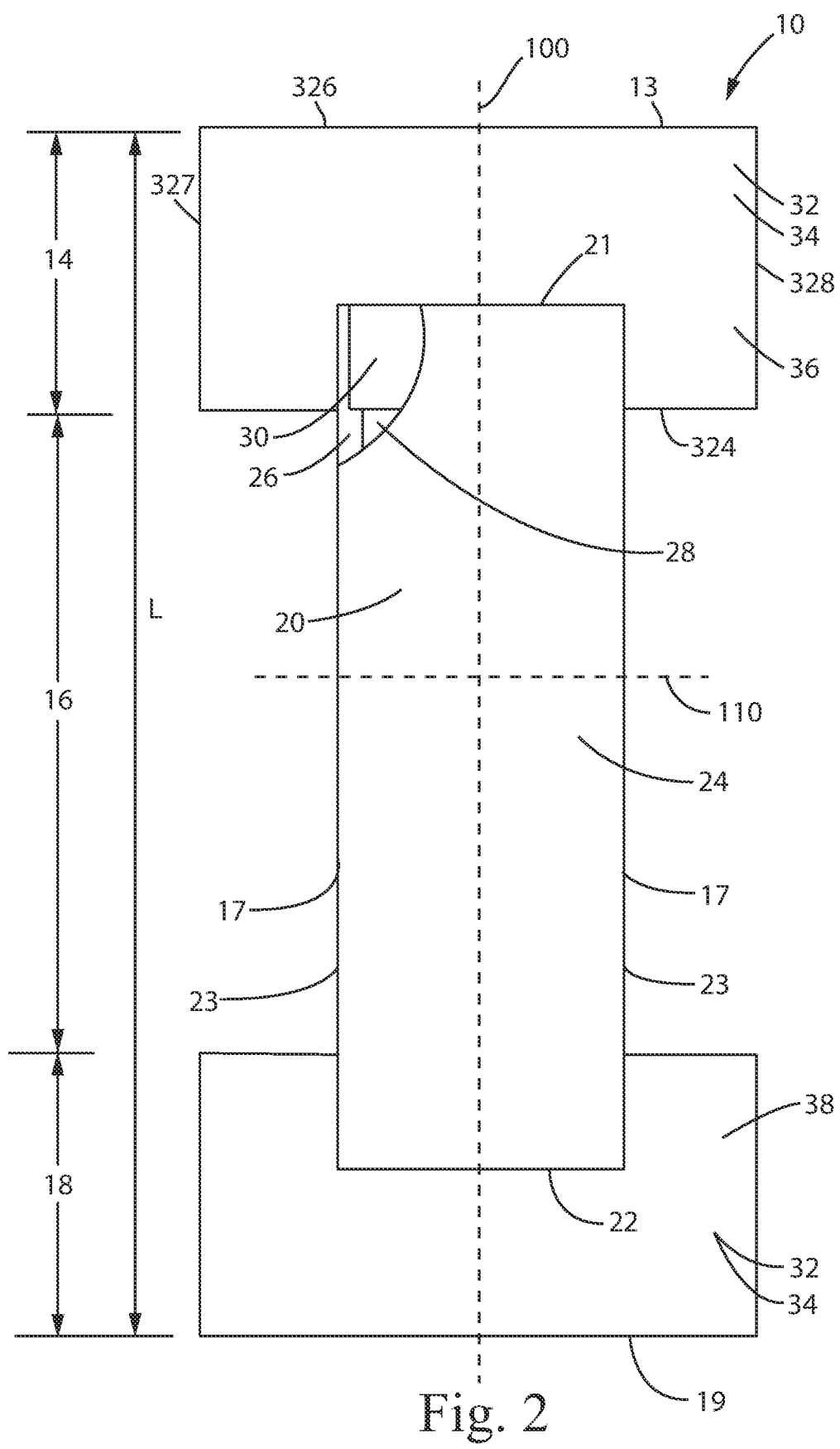
FIG. 2 is a schematic plan view of an exemplary absorbent pant precursor structure according to a nonlimiting embodiment of the present invention. The structure is shown in a flat, uncontracted state.

FIG. 1 illustrates an exemplary absorbent article 10 in the form of a pant 12. FIG. 2 illustrates a precursor structure to an absorbent pant 12, shown in a flat uncontracted state. As is shown in FIG. 2, the absorbent article 10 comprises a first waist region 14, a second waist region 18 and a crotch region 16 disposed between the first and second waist regions. The article 10 further includes first waist edge 13 and a second waist edge 19 substantially opposite the first waist edge 13, and two longitudinal edges 17. The waist regions 14 and 18 generally comprise those portions of the absorbent article 10 which, when worn, encircle the waist of the wearer. The waist regions 14 and 18 may include elastic members such that they gather about the waist of the wearer to provide improved fit and containment. The crotch region 16 is the portion of the absorbent article 10 which, when the absorbent article 10 is worn, is generally positioned between the legs of the wearer.

The article 10 further comprises a longitudinal centerline 100 and a lateral centerline 110. In addition, the article 10 comprises a maximum length, L, extending between the first and second waist edges. In some embodiments, the maximum length is about 600 mm or less, or about 400 mm or less, or from about 200 mm to about 800 mm, reciting for said range every 10 mm increment therein. Lengths herein are measured when the article is in a flat uncontracted state. For irregular shapes, where the outermost points on opposing edges may not be aligned, a maximum length is the distance between those outermost points as measured parallel to the longitudinal centerline. In other words, the maximum length is measured as if the outermost points were aligned.

The article 10 also comprises a chassis 20, which may comprise a liquid permeable topsheet 24, a backsheet 26, and an absorbent core 28 between the topsheet 24 and the backsheet 26. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 30 is disposed between the topsheet 26 and the absorbent core 28.

The chassis 20 may comprise a first lateral chassis edge 21 and a second lateral chassis edge 22. The chassis may also comprise longitudinal chassis edges 23. For at least a portion of the article, the lateral chassis edges 21, 22 may be conterminous with the longitudinal edges 17 of the article.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

The article 10 may further include a waist feature 32 may be joined to the chassis 20 in the first and/or second waist region. The waist feature 32 may extend longitudinally and/or laterally outboard of the chassis in said waist region(s). In further embodiments, the waist feature 32 comprises a belt 34. As illustrated in FIGS. 1 and 2, the belt 34 may comprise a front portion 36 disposed in the first waist region, and a rear portion 38 disposed in the second waist region. In the final assembly of the pant 12, the front belt portion 36 may be joined to the rear belt portion 38 at seams 40, which may be permanent or refastenable. To form the pant 12, the precursor structure may be folded at or about lateral centerline 110 with the topsheet 24 facing inward, and the longitudinal edges of the front 36 and rear 38 belt portions may be joined at seams 40, forming a pant structure having leg openings, front waist edge 13 and rear waist edge 19. In this way, the pant 12 may comprises a pre-formed, continuous waist opening and pre-formed, continuous leg openings for the wearer at the time of donning the pant 12.

Features of the absorbent article are described in further detail below.

Topsheet

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, TN as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635,191; and 5,643,588. The specific examples are not limiting, as any lotion or skin care composition known in the art may be utilized. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core

Figure 3:
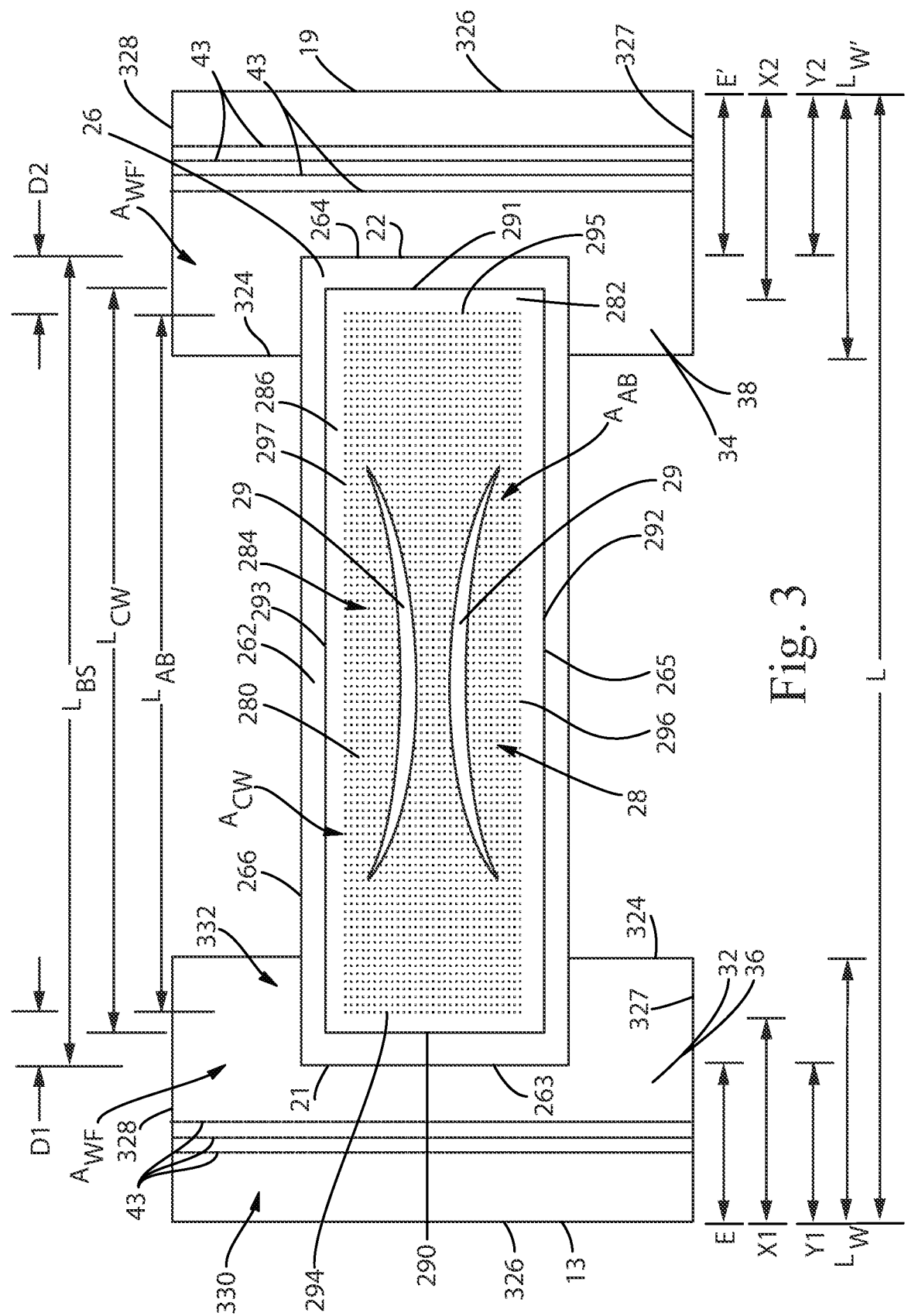
FIG. 3 is a schematic plan view of the exemplary embodiment in FIG. 2 with layers removed to illustrate interior features.
Figure 4:
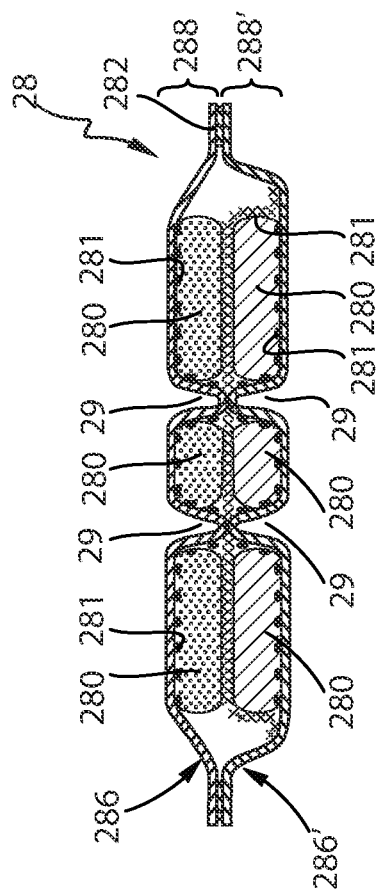
FIG. 4 is a schematic cross sectional view of an exemplary absorbent core in accordance with a nonlimiting embodiment of the present invention.

Turning to FIGS. 3 and 4, the absorbent core 28 is the component of the absorbent article having the most absorbent capacity and comprising an absorbent material and a core wrap or core bag (used interchangeably herein) enclosing absorbent material 280. The term "absorbent core" does not include the acquisition and/or distribution system 30 or any other components of the article which are not either integral part of the core wrap 282 or placed within the core wrap 282. The absorbent core 28 may comprise, consist essentially of, or consist of, a core wrap 282, an absorbent material (e.g., superabsorbent polymers) 280, and optionally one or more adhesives 281.

By "absorbent material," it is meant a material which has some absorbency property or liquid retaining properties, such as superabsorbent polymer material ("SAP"), cellulosic fibers as well as synthetic fibers. Typically, glues used in making absorbent cores have no or little absorbency properties and are not considered as absorbent material. The SAP content may be higher than 80%, for example at least 85%, at least 90%, at least 95%, at least 99%, and even up to and including 100% of the weight of the absorbent material 280 contained within the core wrap 282. This provides a relatively thin core compared to a conventional core typically comprising between 40-60% SAP and high content of cellulose fibers. However, conventional cores are also within the scope of the present disclosure. The absorbent material 280 may comprise about 15% weight percent or less, or about 10% weight percent or less, or about 5% weight percent or less, or about 3% weight percent or less, or about 2% weight percent or less, or about 1% weight percent or less of, or no more than an immaterial amount of, or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers.

"Superabsorbent polymers" ("SAP") as used herein refer to absorbent material which are cross-linked polymeric materials that can absorb at least 10 times their weight of an aqueous 0.9% saline solution as measured using the Centrifuge Retention Capacity (CRC) test (EDANA method WSP 241.2-05E). The SAP used may have a CRC value of more than 20 g/g, more than 24 g/g, from 20 to 50 g/g, from 20 to 40 g/g, or from 24 to 30 g/g, specifically reciting all 0.1 g/g increments within the above-specified ranges and any ranges created therein or thereby. The SAP useful with the present disclosure may include a variety of water-insoluble, but water-swellable polymers capable of absorbing large quantities of fluids. The SAP may be typically in particulate forms (superabsorbent polymer particles), but it not excluded that other forms of SAP may be used such as a superabsorbent polymer foam for example. The absorbent core may thus be relatively thin, in particular thinner than conventional cores comprising cellulosic fibers.

The SAP useful for the present invention may be of numerous shapes, including in particles. The term "particles" refers to granules, fibers, flakes, spheres, powders, platelets and other shapes and forms known to persons skilled in the art of superabsorbent polymer particles. In some embodiments, the SAP particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 μm, and preferably less than 250 μm down to 50 μm. The length of the fibers is preferably about 3 mm to about 100 mm. The fibers can also be in the form of a long filament that can be woven.

Typically, SAP are spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 m, or from 50 to 850 m, preferably from 100 to 710 μm, more preferably from 150 to 650 m, as measured according to EDANA method WSP 220.2-05. SAP having a relatively low particle size help to increase the surface area of the absorbent material which is in contact with liquid exudates and therefore support fast absorption of liquid exudates.

The SAP may have a particle sizes in the range from 45 μm to 4000 μm, more specifically a particle size distribution within the range of from 45 μm to about 2000 μm, or from about 100 μm to about 1000, 850 or 600 μm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass medium particle size up to 2 mm, or between 50 microns and 2 mm or to 1 mm, or preferably from 100 or 200 or 300 or 400 or 500 μm, or to 1000 or to 800 or to 700 μm; as can for example be measured by the method set out in for example EP-A-0,691, 133. In some embodiments of the invention, the superabsorbent polymer material is in the form of particles whereof at least 80% by weight are particles of a size between 50 μm and 1200 μm and having a mass median particle size between any of the range combinations above. In addition, or in another embodiment of the invention, said particles are essentially spherical. In yet another or additional embodiment of the invention the superabsorbent polymer material has a relatively narrow range of particle sizes, e.g. with the majority (e.g. at least 80% or preferably at least 90% or even at least 95% by weight) of particles having a particle size between 50 μm and 1000 μm, preferably between 100 μm and 800 μm, and more preferably between 200 μm and 600 μm.

The absorbent polymer particles can be selected among polyacrylates and polyacrylate based materials that are internally and/or surface cross-linked, such as for example partially neutralized cross-linked polyacrylates or acid polyacrylate. Examples of absorbent polymer particles suitable in the present disclosure are described for instance in the PCT Patent Application WO 07/047598, WO 07/046052, WO2009/155265 and WO2009/155264. Particulate absorbent polymer materials may be made of poly(meth)acrylic acid polymers. However, starch-based particulate absorbent polymer material may also be used, as well as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The absorbent core may comprise one or more types of SAP. Suitable SAP may for example be obtained from inverse phase suspension polymerizations as described in U.S. Pat. Nos. 4,340,706 and 5,849,816 or from spray- or other gas-phase dispersion polymerizations as described in US Patent Applications No. 2009/0192035, 2009/0258994 and 2010/0068520. In some embodiments, suitable SAP may be obtained by processes described in WO 2006/083584.

For most absorbent articles, liquid discharges from a wearer occur predominately in the front half of the absorbent article. The front half of the article (as defined by the region between the front edge 13 and the lateral centerline 110) may therefore comprise most of the absorbent capacity of the core. Thus, at least 60% of the SAP, or at least 65%, 70%, 75%, 80%, or 85% of the SAP may be present in the front half of the absorbent article, while the remaining SAP may be disposed in the rear half of the absorbent article. Alternatively, the SAP distribution may be uniform through the core or may have other suitable distributions.

As shown in FIG. 4, the absorbent material 280 may be disposed on a supporting sheet 286 forming an absorbent layer 288. In some embodiments, the core 28 further comprises a second layer 288' comprising a second supporting sheet 286' having absorbent material 280 deposited thereon. The second absorbent layer may be identical to the first absorbent layer or different (e.g., having different channels, different number of channels, different adhesive, different adhesive application or combinations thereof).

The supporting sheet 286 may surround the absorbent material to form the core wrap 282, or two supporting sheets 286, 286' may be joined to form the core wrap 282 as shown in FIG. 4. In one embodiment, the core wrap 282 may comprise a top layer generally forming the top side of the core 28 and a bottom layer generally forming the bottom side of the core 28. The top and bottom layers may be formed by two separate substrates (e.g., the supporting sheets 286, 286') which may be the same or different material (the top layer being for example hydrophillically treated and/or the bottom layer being for example inherently hydrophobic but air-permeable). There may be a seal along the front edge and back edge of the core wrap 282 for better containment of the absorbent material 280 but many cores do not have such transversal seals. In some embodiments, the top and bottom layer can be attached by gluing or otherwise to form at least one C-wrap seal along each of the longitudinally-extending side edges of the core. However, any other known core wrap constructions may also be used, for example wherein the core wrap is formed of a single web wrapped around the absorbent material with one single longitudinal seal.

The core wrap 282 may be formed by any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 or US2011/0250413A1. Nonwoven materials provided from synthetic fibers may be used, such as PE, PET and in particular PP.

Returning to FIG. 3, the core wrap 282 comprises a maximum length, $L_{CW}$, extending between a first core wrap lateral edge 290 and a second core wrap lateral edge 291. The core wrap may further comprise two longitudinal edges 292, 293. For the avoidance of doubt, "edge" as used herein means the most outermost portion of the component. Thus, for components such as the core wrap which may form a three-dimensional structure, the edges are those that are the outside perimeter limits of the component—not merely where the component changes surface elevations. The core wrap further comprises a core wrap area, $A_{CW}$, which is the two-dimensional mathematical area within the core wrap perimeter.

The absorbent material 280 defines an absorbent material deposition area 284 as seen from above within the plane of the core 28 as shown on FIG. 3. The absorbent material deposition area 284 can be generally rectangular, for example as shown in FIG. 3, but other shapes can also be used such as a "T" or "Y" or "sand-hour" or "dog-bone" shape. In particular the deposition area may show a tapering along its width at the crotch region 16. In this way, the absorbent material deposition area 284 may have a relatively narrow width in an area of the core 280 intended to be placed in the crotch region. This may provide for example better wearing comfort.

The absorbent material deposition area 284 may be defined by a first absorbent area lateral edge 294, a second absorbent area lateral edge 295 that is substantially opposite the first absorbent area lateral edge, a first absorbent area longitudinal edge 296 and a second absorbent area longitudinal edge 297 that is substantially opposite the first absorbent area longitudinal edge. The absorbent material deposition area further comprises a maximum length, $L_{AB}$, extending between the first and second absorbent area lateral edges. The absorbent material deposition area may further comprise an absorbent area, $A_{AB}$, which is the two-dimensional mathematical area within the perimeter of the absorbent material deposition area. For the avoidance of doubt, the absorbent material deposition area may be any suitable shape, including non-rectangular shapes. As such, the absorbent area is determined according to known mathematical area calculations for determining the area of a shape. In some embodiments, the maximum length of the absorbent area, $L_{AB}$, is less than or equal to the length of the core wrap, $L_{CW}$. Likewise, the absorbent area, $A_{AB}$, may be less than or equal to the core wrap area, $A_{CW}$.

In some embodiments (illustrated in FIGS. 3 and 4), the absorbent core 28 may comprise one or more channels 29 that are substantially free of (e.g., free of) superabsorbent polymer material in an absorbent layer 288. It should be understood that, accidentally, a small, negligible amount of superabsorbent polymer particles may be present in the channel, which does not contribute to the overall functionality. Hereinafter, the following the plural form "channels" will be used to mean "at least one channel".

The channels may be formed by zones within the absorbent material deposition area which may be substantially free of absorbent material 280, in particular SAP. In addition or alternatively, the channel(s) may also be formed by continuously or discontinuously bonding the top side of the core wrap to the bottom side of the core wrap through the absorbent material deposition area. The channels may be continuous, but it is not excluded that the channels are intermittent. In embodiments where the absorbent layer 288 comprises cellulosic or cellulose, the channels 29 also may be free of such cellulosic/cellulose material. Further, the channels 29 may extend through the thickness (height) of the absorbent layer 288.

The channels 29 may extend substantially longitudinally, which means typically that the channels 29 extend more in the longitudinal dimension than in the transverse dimension, and typically at least twice as much in the longitudinal dimension than in the transverse dimension. Thus, this includes channels 29 that are substantially parallel to the longitudinal centerline 100; and this includes channels 29 that may be curved, provided the radius of curvature is typically at least equal to the average transverse dimension of the absorbent layer (optionally at least 1.5 or at least 2.0 times this average transverse dimension); and this includes channels 29 that are straight but under an angle of from about 5° to about 30°, or up to about 20°, or up to about 100 with a line parallel to the longitudinal centerline 100. This may also include channels with an angle therein, provided said angle between two parts of a channel is at least 120°, at least 150°; and in any of these cases, provided the longitudinal extension of the channel is more than the transverse extension. In some embodiments, there may be no completely or substantially transverse channels present in at least said crotch region 16, or no such channels at all.

The channels 29 may be present at least in the crotch region 16. The channels may also extend from the crotch region or be present in one or both waist regions. The core 28 may comprise two or more channels 29. In some embodiments, the core 28 may comprise one or more pairs of channels symmetrically arranged relative to the longitudinal axis 100.

In some embodiments, there is no channel that coincides with the longitudinal axis 100. When present as symmetrical pairs relative to the longitudinal axis, the channels may be spaced apart from one another over their whole longitudinal dimension. The smallest spacing distance may be for example at least 5 mm, or at least 10 mm, or at least 16 mm. Furthermore, in order to reduce the risk of fluid leakages, the channels 29 typically do not extend up to any of the edges of the absorbent material deposition area, and are therefore fully encompassed within the absorbent material deposition area 284. Typically, the smallest distance between a channel and the closest edge of the absorbent material deposition area is at least 5 mm.

At least some or all the channels are advantageously permanent channels, meaning their integrity is at least partially maintained both in the dry state and in the wet state. Permanent channels may be obtained by provision of one or more adhesive materials or other bonding technique to adhere for example a supporting layer 286 within the walls of the channel. Permanent channels may be also in particular formed by bonding the top side and bottom side of the core wrap (e.g. first substrate 286 and the second substrate 286') together through the channels. Typically, an adhesive can be used to bond both sides of the core wrap through the channels, but it is possible to bond via other known means, such as pressure bonding, ultrasonic bonding or heat bonding or combination thereof. The core wrap can be continuously bonded or intermittently bonded along the channels. In further embodiments, a channel may be visible through the topsheet and/or through the backsheet. In some embodiments, the channels are visible when viewing the topsheet 24 prior to use. In further embodiments, the channels are visible when viewing the backsheet and/or when viewing the topsheet after the article loaded with a fluid as disclosed in the Wet Channel Saturation Test herein. This may be obtained by making the channels substantially free of SAP, so they will not swell, and sufficiently large so that they will not close when wet. Furthermore bonding the core wrap to itself through the channels may be advantageous. By visible, it is meant that the channels are recognizable by the human eye having 20/20 vision by their shape, outline, changes in the structure of the article (e.g., indentations and/or protuberances form), or otherwise.

Where channels 29 are present in more than one absorbent layer, said channels may be aligned as in FIG. 4 or may not be aligned. The acquisition-distribution system 30 or any sub-layer between topsheet 24 and absorbent core 28, or another layer of the article, may also comprise channels, which may or not correspond to the channels of the absorbent core.

The total amount of SAP present in the absorbent core may also vary according to expected user. The amount of SAP in the core may be from about 5 to about 50 g, or from about 5 to 20 g, specifically reciting all 0.1 increments within the specified ranges and any ranged formed therein or thereby. The average SAP basis weight within the (or "at least one", if several are present) deposition area 284 of the SAP may be at least 50, 100, 200, 300, 400, 500 g/m² or more. The areas of the channels 29 present in the absorbent material deposition area 284 are deducted from the absorbent material deposition area to calculate this average basis weight.

The basis weight (amount deposited per unit of surface) of the SAP may also be varied along the deposition area 284 to create a profiled distribution of absorbent material, in particular SAP, in the longitudinal direction, in the transversal direction, or both directions of the core. Hence along the longitudinal axis of the core, the basis weight of absorbent material may vary, as well as along the transversal axis, or any axis parallel to any of these axes. The basis weight of SAP in area of relatively high basis weight may thus be for example at least 10%, or 20%, or 30%, or 40%, or 50% higher than in an area of relatively low basis weight. In particular the SAP present in the absorbent material deposition area in one or more portions of the crotch region may have more SAP per unit of surface deposited as compared to another area of the absorbent material deposition area 284.

The article 10 may have a total absorbent capacity of about 150 g or greater, or about 200 g or greater, or about 250 g or greater as measured by CRC method referenced above.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Nos. 13/491,642 and 62/210,100

Backsheet

The backsheet 26 is generally positioned such that it may be at least a portion of the garment-facing surface of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. Suitable backsheet 26 materials include films such as those manufactured by Tredegar Industries Inc. of Terre Haute, IN and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, TX, under the designation EXXAIRE. Suitable breathable composite materials comprising polymer blends are available from Clopay Corporation, Cincinnati, OH under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Figure 5A:
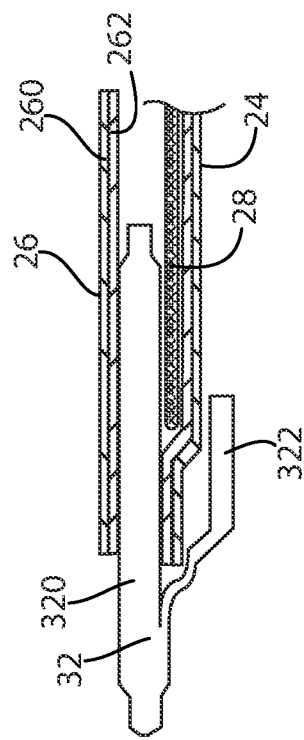
FIGS. 5A-5B are schematic, partial side elevation views of exemplary embodiments of waist features.
Figure 5B:
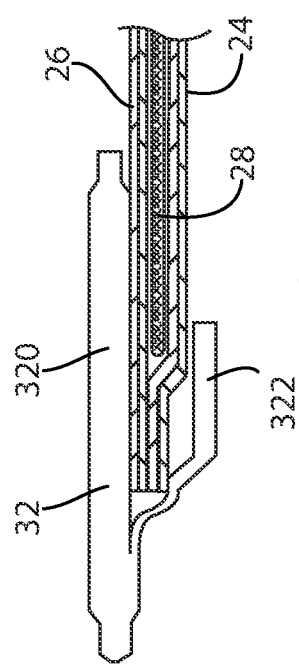

Backsheet 26 may also consist of more than one layer as shown for example in FIG. 5B. The backsheet 26 may comprise an outer cover 260 and a barrier layer 262. The outer cover 262 may be made of a soft, nonwoven material. The barrier layer 262 may be made of a substantially liquid-impermeable film, such as a polymeric film. The outer cover and a barrier layer may be joined together by one or more bonds 261, which may be formed by adhesive or any other suitable material or method. A particularly suitable outer cover is available from Corovin GmbH, Peine, Germany as supplier code A18AH0, and a particularly suitable barrier layer is available from RKW Gronau GmbH, Gronau, Germany as supplier code PGBR4WPR.

In some embodiments where the article 10 comprises a waist feature 32, the outer cover 260 extends beyond the chassis to cover portions of the waist feature 32 or the entirety of the waist feature 32. In further embodiments, the perimeter of the barrier layer 262 may define the perimeter of the chassis 20. In embodiments comprising a single-layer backsheet, the perimeter of the backsheet 26 may define the perimeter of the chassis 20.

Returning to FIG. 3, the barrier layer 262 may comprise a maximum barrier layer length, $L_{BS}$, extending between the first lateral edge 263 of the barrier layer and the second lateral edge 264 of the barrier layer. The barrier layer 262 may further comprise two opposing longitudinal edges 265, 266. In further embodiments, the barrier layer comprises a barrier layer area, $A_{BS}$, which is the two-dimensional mathematical area within the barrier layer perimeter. In embodiments comprising a single-layer backsheet, liquid impermeable area of the backsheet is used when determining the barrier layer length, $L_{BS}$, and area, $A_{BS}$. In some embodiments, the maximum length of the barrier layer, $L_{BS}$, is about 90% or less, or about 80% or less, or about 75% or less, or from about 50% to about 90%, or from about 60 to about 80% of the maximum length of the article, reciting for each range every 5% increment therein.

While a variety of backsheet configurations are contemplated herein, it would be obvious to those skilled in the art that various other changes and modifications can be made without departing from the spirit and scope of the invention.

Waist Feature

As shown in various figures, the absorbent article 10 may include at least one waist feature 32 attached to the chassis 20. The waist feature 32 may comprise breathable materials, permitting air and/or vapors to move through the waist feature and thereby increasing comfort for the wearer. In some embodiments, the waist feature is breathable and is, in some embodiments, more breathable than the backsheet. In nonlimiting examples, the waist feature is at least twice as breathable, or at least 5 times as breathable, or about 10 times as breathable, or about 100× as breathable or from about 2× to about 200×, or about 5× to about 100× as breathable as the backsheet, reciting for each range every 2 increment therein. The waist feature 32 may be water permeable. In some embodiments, at least a portion of the waist feature is apertured. Alternatively, the waist feature 32 may be water impermeable.

Figure 7:
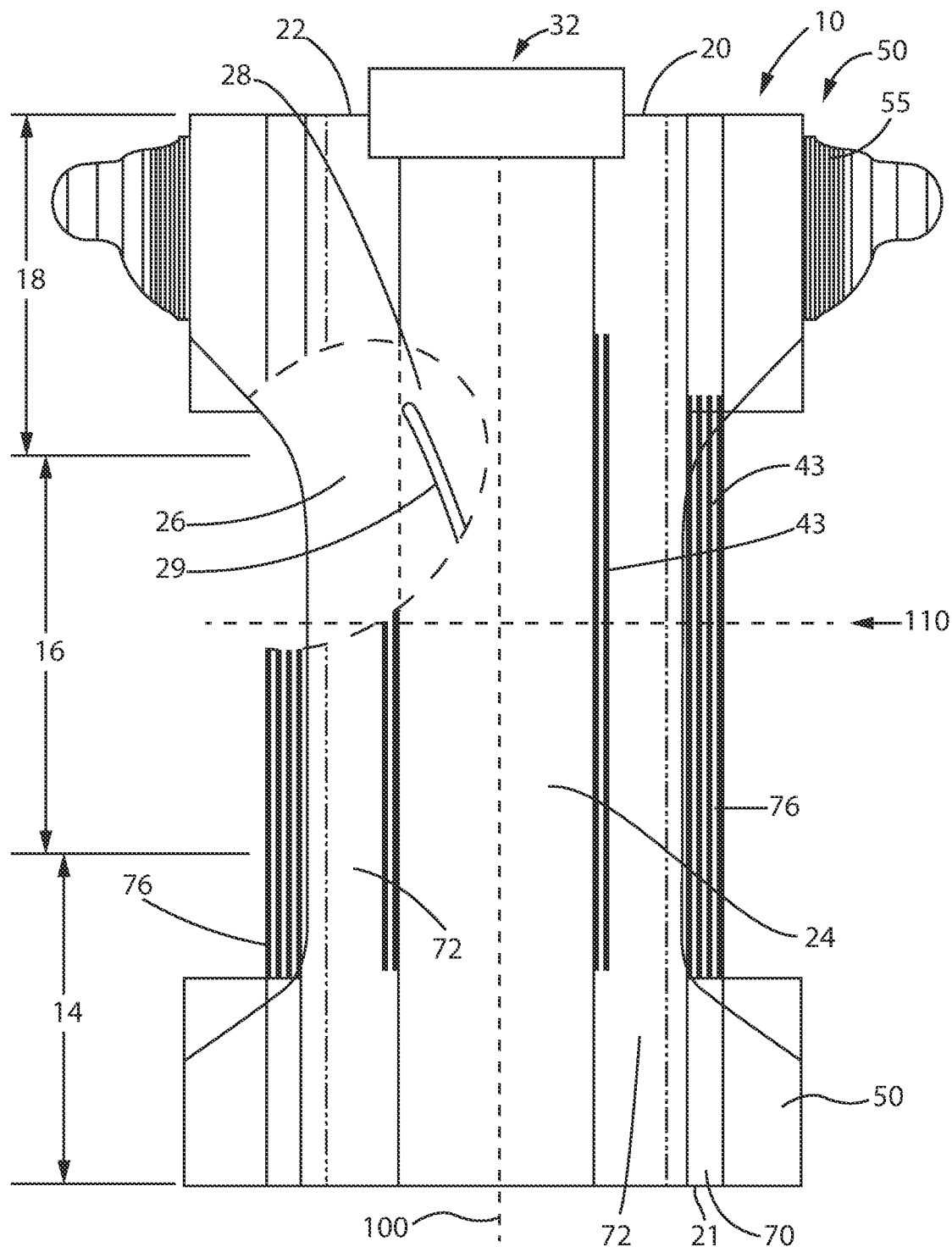
FIG. 7 is a schematic plan view of an exemplary absorbent article according a nonlimiting embodiment of the present invention.

The waist feature 32 may be disposed on the body facing side of the chassis or a body facing side of a layer of the chassis 20 (see FIG. 7). Alternatively, the waist feature 32 may be disposed on the garment facing side of the chassis (see FIG. 2) or a garment facing side of a layer of the chassis 20. In another embodiment, the waist feature 32 may be disposed between layers of the chassis or around layers of the chassis as shown in FIGS. 5A-5B.

Still referring to FIGS. 5A and 5B, the waist feature 32 may comprise a nonwoven, a film, a laminate of nonwovens and/or films, or combinations thereof. In one embodiment, the waist feature 32 comprises a single, continuous web of material and may be formed by folding the single, continuous web. In other embodiments, the waist feature(s) 32 may be formed from more than one web of material (e.g., multiple webs of material that are joined together to become one web of material, or multiple distinct webs of material that are separate from the disposable absorbent article chassis and form part of the waist feature). In embodiments comprising a laminate, an inner layer may be a formed form a different web of material than that of the outer layer. The component materials in the distinct webs may be the same or they may be different. In some embodiments, neither the inner layer nor the outer layer is integral with the chassis (i.e., the waist feature is discrete from the chassis).

In some embodiments, the waist feature 32 is disposed on multiple surfaces of the chassis or layers within the chassis. For example, the waist feature may comprise a garment-facing portion 320 that overlaps a portion of the chassis and/or a body-facing portion 322 that overlaps a portion of the chassis. The waist feature may comprise two separate webs of material which sandwich the chassis, or one web of material which is folded such that it wraps around the chassis (FIG. 5A) or layers within the chassis (FIG. 5B). The waist feature may at least partially surround the core. In certain embodiments, the waist feature is folded to at least partially surround the core.

The waist feature 32 includes an inboard lateral edge 324, an outboard lateral edge 326, and two longitudinal edges 327, 328 as shown for example in FIGS. 2 and 3. In embodiments where the waist feature comprises a belt, each belt portion 36, 38 may comprise an inboard lateral edge 324, an outboard lateral edge 326, and two longitudinal edges 327, 328. The belt portions may have one or more dimensions that are the same and/or one or more dimensions that differ. The waist feature, including belt portions, may comprises any suitable shape, including but not limited to rectangular, non-rectangular, and/or tapered shapes.

The outboard lateral edge 326 may be disposed a longitudinal distance E away from a proximate barrier lateral edge as shown in FIG. 3. In nonlimiting examples, E is about 10 mm or greater, or about 15 mm or greater, or about 20 mm or greater, or about 20 mm to about 100 mm, reciting for said range every 5 mm increment therein. The waist feature may comprise a length, $L_W$, extending between its inboard lateral edge and its outboard lateral edge. In some embodiments, for example in taped diaper embodiments, the waist feature length, $L_W$, may be about 15 mm or greater, or about 20 mm or greater, or about 25 mm or greater, or about 30 or greater, or from about 15 mm to about 150 mm, or from about 30 mm to about 100 mm, reciting for each range every 5 mm increment therein. In further embodiments, for example in absorbent pant embodiments, the waist feature length, $L_W$, may be about 75 mm or greater, or about 100 mm or greater, or from about 50 mm to about 250 mm, or from about 75 mm to about 200 mm. The periphery of the waist feature (e.g., the lateral and longitudinal edges) defines a waist feature area, $A_{WF}$ (i.e., the mathematical, two-dimensional area of the waist feature). The area of belt portions ($A_{WF}$, $A_{WF}'$) may be the same or may differ. Front and rear belt portions may have the same or different $L_W$, $L_W'$. In some embodiments having a belt, the rear belt portion 38 may have a greater length, $L_W'$, than the length of the front belt portion 36, $L_W$. This may help provide greater coverage of the wearer's buttocks area in the rear while providing greater comfort in front, via better conformity with wearer anatomy and natural body movement. Further, front and rear belt portions may be disposed at the same or at different distance from their respective proximate barrier lateral edges (i.e., E may equal E' or E may be different from E').

In an embodiment, the waist feature 32 comprises a waist feature pocket 33 as shown in FIG. 5A, for example. The pocket 33 may be formed from a portion of the waist feature 32 that is unattached from the chassis 20.

Figure 6:
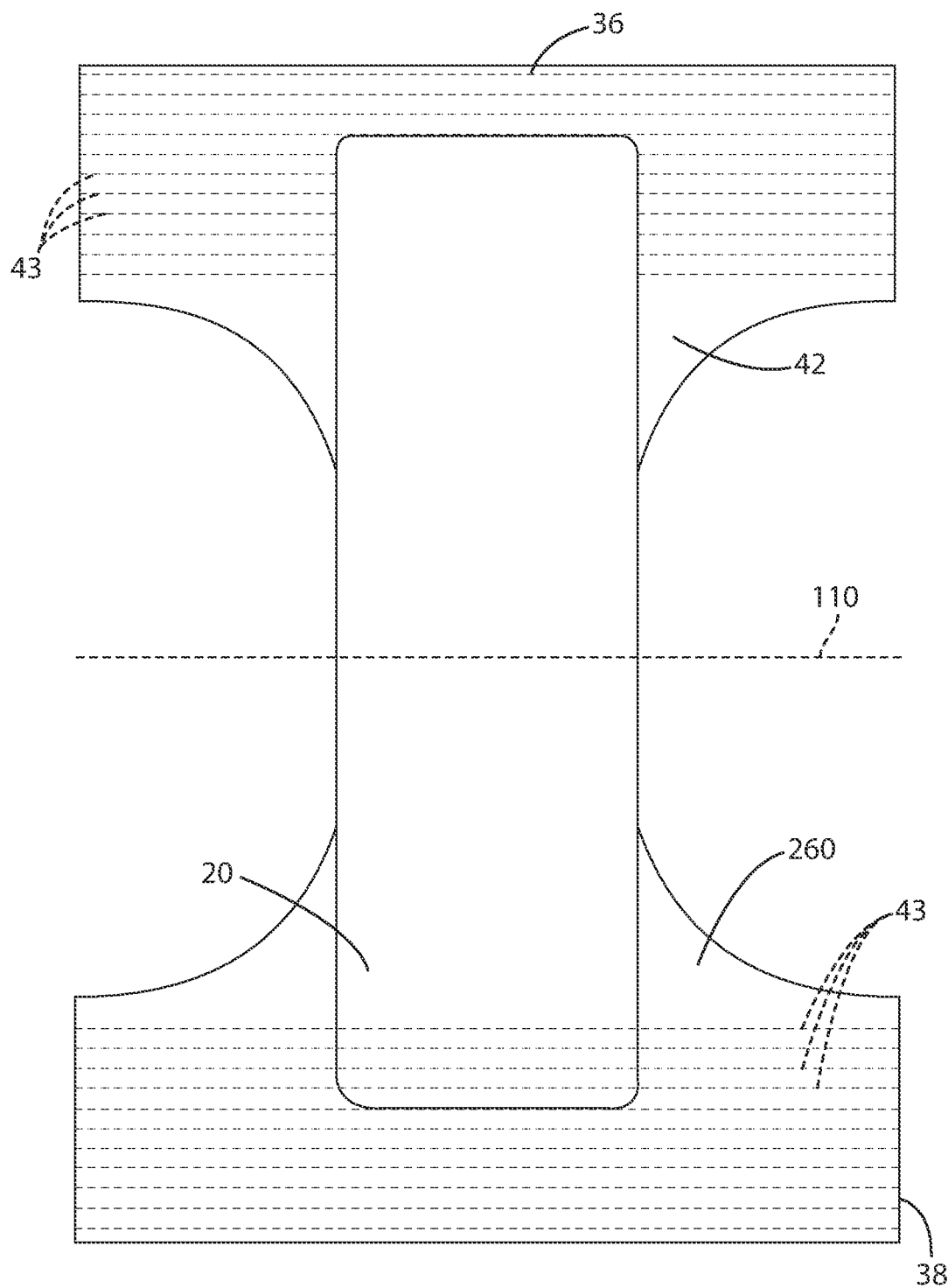
FIG. 6 is a schematic plan view of an exemplary absorbent pant precursor structure according to a nonlimiting embodiment of the present invention.

Turning to FIG. 6, the waist feature 32 may comprise a belt 34, which may have front and rear belt portions 36, 38. The front and rear belt portions 36, 38 may be the outermost structures forming the front and rear regions of a pant 12. The pant may include an outer wrap 42 wrapping the entirety of the front, crotch and rear regions, and forming an outermost pant-shaped structure. In some embodiments, the outer cover 260 of the backsheet forms the outer wrap. Additional layer(s) and elastic members 43 to form front and rear belt portions 36, 38 may be disposed to the inside of outer wrap 42, and be suitably affixed thereto by adhesive lamination, bonding or any other suitable mechanism. An outer wrap 42 may be formed of one or more sections of nonwoven web and may be cut to a profile providing suitably tailored leg opening edge profiles as desired.

The waist feature 32, including one or both of front and rear belt portions 36, 38, may be formed of layers of nonwoven web. Suitable nonwoven web materials that may be useful in the present invention also include, but are not limited to spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers, as known in the art. The nonwoven web may be formed predominately of polymeric fibers. In some examples, suitable nonwoven fiber materials may include, but are not limited to polymeric materials such as polyolefins, polyesters, polyamide, or specifically, polypropylene (PP), polyethylene (PE), poly-lactic acid (PLA), polyethylene terephthalate (PET) and/or blends thereof. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933; and 7,112,621; and in U.S. patent application Ser. Nos. 10/338,603; 10/338,610; and Ser. No. 13/005,237. The individual fibers of a nonwoven layer may be monocomponent or multicomponent (including bicomponent). The multicomponent fibers may be bicomponent, with differing polymeric components in, e.g., a core-and-sheath or side-by-side arrangement. The individual components may include polyolefins such as polypropylene or polyethylene, or their copolymers, or polyesters, thermoplastic polysaccharides or other biopolymers.

According to some nonlimiting examples, the nonwoven used for a belt portion may include a material that provides good recovery when external pressure is applied and removed. Further the nonwoven may include a blend of different fibers selected, for example from the types of polymeric fibers described above. In some examples, at least a portion of the fibers may exhibit a spiral curl which has a helical shape. According to one example, the fibers may include bicomponent fibers, which are individual fibers each including different materials, usually a first and a second polymeric material. It is believed that the use of side-by-side bi-component fibers is beneficial for imparting a spiral curl to the fibers. Examples of potentially suitable curled or "crimped" bicomponent fibers and nonwovens formed from them are described in U.S. Pat. Nos. 5,382,400; 5,418,045; 5,707,468; 6,454,989; 6,632,386; 5,622,772 and 7,291,239. For purposes herein, use of a nonwoven formed of crimped bicomponent or multicomponent fibers such as, for example, described in the patents and/or patent applications cited immediately above, may be desired as one or more layers used to form the belt portions, because they can feel particularly soft to the touch (for wearer comfort on the inside and aesthetically pleasing feel on the outside) and are generally quite pliable.

The waist feature 32 may further comprise one or more elastic members 43. The elastic members 43 may be elastomeric fibers, such as LYCRA® fibers available from INVISTA of Wichita, KS, in various decitex levels. The elastic members 43 may also comprise any heat shrinkable elastic material as is well known in the art. Other suitable elastics can be made various other materials including but not limited to: rubbers, styrene ethylbutylene styrene, styrene ethylene propylene styrene, styrene ethylene propylene styrene, styrene butadiene styrene, styrene isoprene styrene, polyolefin elastomers, elastomeric polyurethanes, and other elastomeric materials known in the art, and combinations thereof. In some nonlimiting examples, the elastic members may be extruded strand elastics with any number of strands (or filaments). In some embodiments, the elastic members can have a decitex ranging from 50 to 2000, or any integer value for any decitex value in this range. However, the skilled person may select the appropriate decitex based on the desired contraction and other principles discussed herein. In further embodiments, the elastic members may be in a form of film. Examples of films have been described in prior patent applications (see, for example, U.S. Pat. App. Pub. No. 2010/0040826). The film may be created with a variety of resins combined in at least one of several sublayers, the latter providing different benefits to the film.

In addition, elastic members 43 may take a multitude of configurations. For example, the width may be varied; a single strand or several parallel or non-parallel strands of elastic material may be used; or a variety of shapes may be used including rectilinear and curvilinear; or a variety of cross sectional shapes can be used (circular, rectangular, square, etc.).

Layers of the waist feature 32 and/or chassis 20 may be joined together about elastic strands 43 by adhesive deposited between the layers, by thermal bonds, by compression bonds, or by a combination thereof. In other examples, the one or more elastic members may be strips or a section of film formed of elastomeric material. Where the elastic member is elongate, it may be desirable that the longer dimension be laterally oriented, or even substantially aligned with the lateral direction, as strands 43 are depicted in FIG. 6 for example.

The waist feature 32 may comprise at least 3 waist elastic members 43, at least 5 elastic members 43, at least 10 waist elastic members 43, or at least 15 waist elastic members 43, or from about 2 to about 35 waist elastic members, or from about 5 to about 25 waist elastic members, reciting for each range every 1 increment therein.

In one embodiment, adjacent elastic members 43 are spaced a longitudinal distance of at least 3.5 mm apart from one edge of the member to the other edge of the member, optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The spacing between elastic members may be the same or different across the longitudinal length of the waist feature. For example, the spacing between adjacent elastic members could uniformly be 7 mm or there could be variable spacing (i.e., two adjacent elastic members are separated by 3 mm, another two are separated by 6.5 mm, etc.).

During manufacture of the waist feature, the elastic members 43 may be pre-strained by a desired amount as they are being incorporated into the waist feature. Upon subsequent relaxation of the waist feature, the elastic members will contract laterally toward their unstrained lengths. This may cause layers of the waist feature to gather and form ruffles or rugosities having ridges and valleys generally transverse to the lengths of the elastic members 43, and extending in the z-direction.

In further embodiments, to adhere the components of the waist feature laminate, the elastic members may be individually coated with adhesive ("strand coated") prior to incorporation into the waist laminate. Various coating methods and techniques, including strand coating methods and techniques, are shown for example in U.S. Pat. Nos. 5,340,648; 5,501,756; 5,507,909; 6,077,375; 6,200,635; 6,235,137; 6,361,634; 6,561,430; 6,520,237; 6,582,518; 6,610,161; 6,613,146, 6,652,693, 6,719,846 and 6,737,102. The adhesive used may be a hot-melt type adhesive having elasticity and flexibility making it suitable for attaching pre-strained elastic materials to substrates, such as OMNIMELT BLOCKS 22 H2401F, or ZEROCREEP brands such as AVANCE, available from Bostik, Inc., Wauwatosa, Wisconsin.

In certain embodiments, corners of the front and/or rear belt portion may be trimmed off as suggested in FIG. 6. The corners may be trimmed off along straight lines, or may be trimmed off along trim paths that are curved and either concave or convex with respect to the remaining area of the belt portion (see FIG. 6), as may be desired to impart a particular curved leg edge profile. In conjunction with such trimming and the configuration of elastic strands described above, it may be desired to impart bonding between layers along edges of the respective belt portion 36, 38. Such bonding may serve to prevent any separation of the layers along edges that may contribute to creating a ragged appearance, and may also help the rear belt portion more effectively draw inward laterally toward the central chassis 20, under the contractive force of the elastic strands below seams 40. Bonding may be effected by mechanical/compression bonds as described in, for example, U.S. Pat. Nos. 4,854,984 and 4,919,738, by thermal bonds or welds, or by deposits of adhesive between layers. In nonlimiting examples, such bonding may form a pattern along edges. Such bonding may be supplemental to any bonding between layers generally holding the respective belt portion 36, 38 together as a laminate structure.

Side seams 40 may be permanent or refastenable. Permanent seams may be formed between the front belt portion and the rear belt portion by any bonding mechanism wherein the front and rear belt portions may not be forcibly separated without substantial damage to one or both of the front and rear belt portions, or without any included mechanism by which substantial reattachment or refastening may be effected. Bonding forming permanent seams may include compression bonding, thermal bonding/welds, ultrasonic bonding or adhesive bonding. Refastenable seams may be formed between the front belt portion and the rear belt portion by any mechanism configured to permit substantially non-destructive forcible separation of the front and rear belt portions, and subsequent substantial reattachment or refastening at the same locations. One example of such mechanism is a hook-and-loop fastening system, for example, a VELCRO fastening system. A suitably sized and shaped hooks component may be bonded to one of the front or rear belt portions along the longitudinal edges thereof, and a suitably sized and shaped loops component may be bonded to the other of the front or rear belt portions along the longitudinal edges thereof, in positions in which they may be brought together and engaged to form seams 40. Examples are depicted in U.S. Pat. App. Serial Nos. 61/787,416; 61/787,332; 61/666,065.

As mentioned above in reference to FIG. 3, the outboard edge 326 of the waist feature 32 may extend beyond a barrier layer lateral edge 263. In this regard, the waist feature may comprise a free portion 330 and an overlapping portion 332 as depicted in FIG. 3. The free portion 330 may comprises the length, E, which may be about 10 mm or greater, or about 15 mm or greater, or about 20 mm or greater, or about 20 mm to about 100 mm, reciting for said range every 5 mm increment therein. In some embodiments, the overlapping portion 332 may comprise a greater force than the free portion. Waist features designed according to the present teachings comprise less excess material (e.g., in the backsheet and core), which can reduce the amount of contraction force necessary when compared to known waist features. Typically, waist features provide tight elastic contact around the wearer, leading to skin irritation and discomfort. The decreased force in the free portion lessens the pressure exerted by elastics on the wearer, and thereby increases comfort and decreases the potential for skin irritation. Non-limiting examples of ways by which the force differential is created include greater applied strain levels on the inboard elastic member(s), greater decitex of the inboard elastic member(s), greater diameter of the inboard elastic member(s), different base materials between inboard and outboard elastic members (i.e., such that an inboard elastic member has a higher Young's modulus or stiffness), more elastic members disposed inboard than outboard, and closer longitudinal spacing between adjacent elastic members that are inboard versus elastic members disposed more outboard.

While features may be described with respect to one waist feature or one belt portion herein, it is also contemplated that a second waist feature and/or a second belt portion may also comprise said features, including but not limited to free portions, overlapping portions, aforementioned lengths, elastic members, and differential force. Multiple waist features and/or different belt portions may comprise substantially the same features and/or differences amongst their features (e.g., a rear waist portion may comprise a free portion having a greater length than the free portion of a front waist portion).

Ears

The absorbent article 10 may include front ears and/or back ears 50. The ears may be extensible, inextensible, elastic, or inelastic. The ears 50 may be integral with the chassis and/or waist feature. Alternatively, the ears may be discrete from the chassis and/or waist feature. The ears 50 may be formed from nonwoven webs, woven webs, knitted fabrics, polymeric and elastomeric films, apertured films, sponges, foams, scrims, and combinations and laminates thereof. In some embodiments, the ear may include elastomers (e.g., elastic strands, LYCRA© fibers), such that the ear is stretchable. In certain embodiments, the ears may be formed of a stretch laminate such as a nonwoven/elastomeric material laminate or a nonwoven/elastomeric material/nonwoven laminate, which also results in the ear being stretchable. Stretch laminates may be formed by any method known in the art. For example, the ears may be formed as a zero strain stretch laminate, which includes at least a layer of nonwoven material and an elastomeric element. The elastomeric element is attached to the layer of nonwoven material while in a relaxed or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 20, in which case the elastomeric element may be attached to the nonwoven layer and the nonwoven/elastomeric element laminate is subsequently activated. Alternatively, the nonwoven layer may be a separate component, in which case the elastomeric element is attached to the nonwoven layer to form the laminate, which is then coupled to the main portion. If one or more layers of the ear 50 are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, VA, as supplier code X25007) disposed between two nonwoven layers (such as is available from BBA Fiberweb, Brentwood, TN as supplier code FPN332).

An ear 50 may be highly extensible wherein the ear 50 is capable of extending up to 150%. It is believed that highly extensible ears 50 allow an absorbent article 10 to expand to comfortably fit a range of wearers who vary in shape and/or weight. Suitable highly extensible ears are described in U.S. Pat. Nos. 4,116,892; 4,834,741; 5,143,679; 5,156,793; 5,167,897; and 5,422,172; and 5,518,801; PCT App. No. WO 2005/110731; and U.S. App. Nos. US 2004/0181200 and US 2004/0193133.

Fasteners

The absorbent article 10 may also include a fastening system 55 as shown in FIG. 7. When fastened, the fastening system 55 interconnects the first waist region 16 and the rear waist region 18 resulting in a waist circumference that may encircle the wearer during wear of the absorbent article 10. The fastening system 55 may comprise tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 55 may also provide a means for holding the article in a disposal configuration as disclosed in U.S. Pat. No. 4,963,140. The fastening system 36 may also include primary and secondary fastening systems, as disclosed in U.S. Pat. No. 4,699,622. The fastening system 55 may be constructed to reduce shifting of overlapped portions or to improve fit as disclosed in U.S. Pat. Nos. 5,242,436; 5,499,978; 5,507,736; and 5,591,152. In some embodiments, the fastening system 36 and/or the fastener 38 is foldable. The fastening system 55 may be joined to any suitable portion of the article 10 by any suitable means. In some embodiments, the fastening system is joined to a belt 34. In other embodiments, the fastening system is joined to an ear 50.

Leg Gasketing System

The absorbent article 10 may comprise a leg gasketing system 70 attached to the chassis 20, which may comprise one or more cuffs as shown in FIG. 1 and FIG. 7. In the embodiment suggested by FIG. 7, the leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs may be delimited by a proximal edge joined directly or indirectly to the topsheet 24 and/or the backsheet 26 and a free terminal edge, which is intended to contact and form a seal with the wearer's skin. In some embodiments, the free terminal edge comprises a folded edge. The barrier leg cuffs 72 extend at least partially between the first and second lateral chassis edges 21, 22 on opposite sides of the longitudinal centerline 100 and are at least present in the crotch region. The barrier leg cuffs may be joined at the proximal edge with the chassis of the article by a bond which may be made by gluing, fusion bonding, or a combination of other suitable bonding processes. The barrier leg cuffs may be integral with the topsheet 24 or the backsheet 26 or may be a separate material joined to the article's chassis. Each barrier leg cuff 72 may comprise one, two or more elastic elements 43 close to the free terminal edge to provide a better seal.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximal edge and a free terminal edge. The free terminal edge may comprise a folded edge. Each gasketing cuff may comprise one or more elastic elements 43 in the chassis of the absorbent article between the topsheet 24 and backsheet 26 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134, 622, 14/077,708; U.S. Pat. Nos. 8,939,957; 3, 860,003; 7,435,243; 8,062,279.

Combination of Layers

Returning to FIG. 3, the layers of the article 10 may be combined to maximize the use of space. For example, the layers may be combined to maximize the amount of absorbent area and thereby the amount of absorbency for the size of the article.

In certain embodiments, the maximum length of the absorbent area, $L_{AB}$, is about 80% or greater, or about 85% or greater, or about 90% or greater, or about 95% or greater of the maximum length of the barrier layer, $L_{BS}$. In this way, the space for absorbent material is maximized across the length of the barrier layer. Additionally or alternatively, the maximum length of the core wrap, $L_{CW}$, may be substantially the same as the maximum length of the barrier layer, $L_{BS}$, or about 80% or greater, or about 90% or greater or about 95% or greater, or about 100% of the maximum length of the barrier layer, $L_{BS}$. This also helps to ensure efficient and maximized placement of the absorbent material. In further embodiments, the absorbent area, $A_{AB}$, is about 70% or greater, or about 80% or greater, or about 90% or greater, or from about 70% to about 100% of the barrier layer area, $A_{BS}$, reciting for said range every 5% increment therein. Additionally, or alternatively, the area of the core wrap, $A_{CW}$, is substantially the same as the barrier layer area, $A_{BS}$, or about 80% or greater, or about 90% or greater or about 95% or greater, or about 100% of the barrier layer area, $A_{BS}$.

In still further embodiments, the first absorbent area lateral edge 294 is disposed a distance, D1, from the first barrier layer lateral edge 263. In nonlimiting examples, D1 is about 3% or less, or about 5% or less, or about 10% or less, or from about 2% to about 15% or less of the maximum barrier layer length, $L_{BS}$, reciting for said range every 1% increment therein. In this way, the absorbent material is placed closer to the front of the article where greater saturation is sometimes more likely to occur. Additionally or alternatively, the second absorbent area lateral edge 295 may be disposed a distance, D2, from the second barrier layer lateral edge 264. In nonlimiting examples, D2 is about 3% or less, or about 5% or less, or about 10% or less, or from about 2% to about 15% or less of the maximum barrier layer length, $L_{BS}$, reciting for said range every 1% increment therein. In some embodiments, both D1 and D2 are about 3% or less, or about 5% or less, or about 10% or less, or from about 2% to about 15% of the maximum barrier layer length, $L_{BS}$, reciting for said range every 1% increment therein.

The first absorbent area lateral edge 294 may be disposed a distance, X1, from the first waist edge 13. In some nonlimiting examples, X1 is about 100 mm or less, or about 50 mm or less, or about 30 mm or less, or about 20 mm or less, or from about 20 mm to about 100 mm, reciting for said range every 10 mm increment therein. In further embodiments, the second absorbent area lateral edge 295 may be disposed a distance, X2, from the second waist edge 19. In some nonlimiting examples, X2 is about 20 mm or less, or about 30 mm or less or about 50 mm or less, or from about 20 mm to about 100 mm. The distances X1 and X2 may be the same or may be different. In some embodiments, the waist feature outboard edge 326 comprises the first or second waist edge as shown in FIG. 3.

The first barrier layer lateral edge 263 may be disposed a distance Y1 from the first waist edge 13 and/or the second barrier layer lateral edge 264 may be disposed a distance Y2 from the second waist edge 19. In nonlimiting examples, Y1 and/or Y2 may be about 10 mm or greater, or about 15 mm or greater or about 20 mm or greater, or from about 10 to about 100 mm, or from about 20 mm to about 50 mm, reciting for each range every 10 mm increment therein. The distances Y1 and Y2 may be the same or may be different. In some embodiments, the waist feature outboard edge 326 comprises the first or second waist edge as shown in FIG. 3. In such embodiments, Y1 and/or Y2 may equal E and/or E' respectively. Additionally or alternatively, a barrier layer lateral edge 263, 264 may be coterminous with a chassis lateral edge 21, 22. In other embodiments, a barrier layer lateral edge is not coterminous with a chassis lateral edge.

Each of the foregoing maximizes the absorbent area within the article. The efficient use of space within the article allows for enhanced features, such as channels which improve fit, without compromising absorbency due to the lack of absorbent material where said features exist. Further, the space permits greater amounts of absorbent material to be included without creating additional bulk or density, and greater total absorbency. Likewise, article made according to the teachings herein may have reduced excess backsheet materials, such as barrier layer material; excess materials often indicate product failure, a lack of a secure fit to consumers, and/or may cause excess noise which can be undesirable for wearers, especially wearers of adult incontinence articles. The present teachings also allow for reduction in adhesive or other bonding such as tackdown bonds used to secure leg cuffs. Typically, a leg cuff is bonded to the chassis between the core wrap lateral edge and the waist edge to prevent gaps in the cuffs during wear. Here, because the core is closer to the waist edge, a cuff tackdown bond can be shortened compared to known articles or eliminated, thereby reducing processing steps and/or bonding material costs. Further, the length of the core wrap and/or the length of the absorbent deposition area as prescribed herein may provide a visual assurance that the article will contain exudates. Further still, in embodiments comprising a waist feature pocket 33, the waist feature 32 may stand up and redirect exudates to the core 28. Given the close proximity of the core to the waist feature as disclosed herein, the core will be better able to absorb said exudates.

In further embodiments exemplified in FIGS. 8-9B, the article 10 may comprise one or more sealing portions 210 configured to seal opposing end portions of the absorbent core 28. For example, as shown in FIG. 9A, a first sealing layer 210a may be configured to overlap the first lateral core wrap edge 290 and the first lateral chassis edge 21. In some embodiments, the core wrap edge 290 may be coextensive with the first lateral chassis edge 21. Thus, the first sealing layer 210a may be connected with the topsheet 24 and a portion 322 of the belt that faces the wearer such that the topsheet 24, the backsheet 26, and core wrap 282, are positioned between the inner, wearer facing portion 322 and the first sealing layer 210a. As shown in FIG. 9B, a second sealing layer 210b may be configured to overlap the second core wrap lateral edge 291 and the second chassis lateral edge 22. In some embodiments, the second core wrap lateral edge 291, may be coextensive with the second chassis lateral edge 22. Thus, the second sealing layer 210b may be connected with the topsheet 24 and the inner, wearer facing portion 322 of the elastic belt such that the topsheet 24, the backsheet 26, and the core wrap 282 are positioned between the inner, wearer facing portion 322 and the second sealing layer 210b.

It is to be appreciated that sealing layers 210 may be formed in various ways. For example, as shown in FIGS. 9A and 9B, the first sealing layer 210a may comprise a portion of outer, garment facing portion 320 of the first belt portion 36 that is folded onto the topsheet 24 and placed in a facing relationship with the inner, wearer facing portion 322 of the front belt portion 36. And the second sealing layer 210b may comprise a portion of outer, garment facing portion 320 of the rear belt portion 38 that is folded onto the topsheet 24 and placed in a facing relationship with the inner, wearer facing portion 322 of the rear belt portion 38. It is to be appreciated the sealing layers 210 may be bonded to the inner, wearer facing portion 322 and the topsheet 24 to help prevent absorbent material 280 from migrating or escaping longitudinally from absorbent core 28 from between the first and second supporting layers 286, 286' (i.e., core wrap 282) and/or from between the backsheet 26 and the topsheet 24. As opposed to folding a portion of the front and/or rear belt portions 36, 38 to form the sealing layers, in some configurations, the sealing layers 210 may be formed from a separate strip of material that is bonded to the front and/or rear belt portions.

Articles as disclosed herein may be manufactured in accordance with the teachings of the U.S. Pat. No. 11,096,835, which is commonly assigned to the Procter & Gamble Company.

Combinations:

A. An absorbent article comprising:
  a first waist region, a second waist region, and a crotch region disposed between the first and second waist regions; a longitudinal centerline and a lateral centerline;
  a chassis comprising a topsheet, a backsheet and an absorbent core disposed between the topsheet and the backsheet; and
  a waist feature joined to the chassis in the first and/or second waist region and a portion extending longitudinally outboard of the chassis in said first and/or second waist region to form a free portion;
  wherein:
  the backsheet comprises a barrier layer having a maximum length, $L_{BS}$, extending between a first barrier lateral edge and a second barrier lateral edge;
  the absorbent core comprises absorbent material enclosed in a core wrap having a maximum length, $L_{CW}$, and wherein $L_{CW}$ is substantially the same as $L_{BS}$; and
  the absorbent material is disposed in an absorbent material deposition area, the absorbent material deposition area having a maximum length, $L_{AB}$, extending between a first absorbent area lateral edge and a second absorbent area lateral edge.

B. An absorbent article according to paragraph A wherein $L_{AB}$ is about 90% or greater of $L_{BS}$.

C. An absorbent article according to paragraphs A or B wherein the first absorbent area lateral edge is disposed a longitudinal distance, D1, from the first barrier lateral edge, wherein D1 is 5% or less of $L_{BS}$.

D. An absorbent article according to any of the preceding paragraphs wherein the second absorbent area lateral edge is disposed a longitudinal distance D2 from the second barrier lateral edge, wherein D2 is 5% or less of $L_{BS}$.

E. An absorbent article according to any of the preceding paragraphs wherein the free portion comprises a length E of about 15 mm or greater, or about 20 or greater.

F. An absorbent article according to any of the preceding paragraphs wherein the barrier layer is breathable.

G. An absorbent article according to any of the preceding paragraphs wherein the waist feature is breathable, and optionally the waist feature is more breathable than the barrier layer.

H. An absorbent article according to any of the preceding paragraphs wherein the absorbent material comprises a superabsorbent polymer material.

I. An absorbent article according to any of the preceding paragraphs further comprising a total absorbent capacity of at least about 200 g according to the CRC test method.

J. An absorbent article according to any of the preceding paragraphs wherein the waist feature comprises a pocket.

K. An absorbent article according to any of the preceding paragraphs wherein portions of the waist feature at least partially wrap around the absorbent core.

L. An absorbent article according to any of the preceding paragraphs wherein the article further comprises a fastening system.

M. An absorbent article according to any of the preceding paragraphs wherein the article comprises a pant.

N. An absorbent article according to any of the preceding paragraphs further comprising a maximum length, L, and wherein the maximum length of the barrier layer, $L_{BS}$, is less than about 75% of L and/or wherein the maximum length, L is about 600 mm or less.

O. An absorbent article according any of the preceding paragraphs wherein the first absorbent area lateral edge is within about 50 mm of the first waist edge.

P. An absorbent article according to any of the preceding paragraphs wherein the absorbent material comprises about 15% or less by weight of cellulosic material.

Q. An absorbent article according to any of the preceding paragraphs wherein the waist feature a length, $L_W$, of at least about 25 mm.

R. An absorbent article according to any of the preceding paragraphs wherein the waist feature comprises a side seam.

S. An absorbent article according to any of the preceding paragraphs wherein the absorbent material deposition area comprises an absorbent area and wherein the barrier layer comprises a barrier layer area, and wherein the absorbent area is at least about 90% of the barrier layer area.

Test Methods

Wet Channel Saturation Test

This test is designed to check the visibility of a channel following wet saturation. The test can be performed directly on an absorbent article or on an absorbent core taken separately.

1. The full length (in millimeters) of the channel is measured in the dry state (if the channel is not straight, the curvilinear length through the middle of the channel is measured).

2. The absorbent article or core is then completely immersed in a large excess (e.g. 5 liters) of synthetic urine "Saline", with a concentration of 9.00 g NaCl per 1000 ml solution prepared by dissolving the appropriate amount of sodium chloride in distilled water. The temperature of the solution must be 20+/−5° C.

3. After 1 minute in the saline, the absorbent article or core is removed and held vertically by one end for 5 seconds to drain, then extended flat on an horizontal surface with the wearer (topsheet) side intended to be facing the wearer facing up. If the absorbent article or core comprises stretch elements, it is pulled taut in both X and Y dimensions so that no contraction is observed. The front and back edges of the absorbent article or core are fixed to a horizontal surface, so that no contraction can happen.

4. A channel is viewed by a person having 20/20 vision, aided or unaided.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a first waist region, a second waist region, and a crotch region disposed between the first and second waist regions; a longitudinal centerline and a lateral centerline;
a chassis comprising a topsheet, a backsheet and an absorbent core disposed between the topsheet and the backsheet; and
a waist feature joined to the chassis in at least one of the first waist region and the second waist region, wherein the waist feature comprises a free portion extending longitudinally outboard of the chassis and transversely outboard of the chassis in at least one of the first waist region and the second waist region such that the free portion does not overlap the chassis;
wherein the backsheet comprises an outer cover and a barrier layer,
wherein the barrier layer has a maximum length, $L_{BS}$, extending between a first barrier lateral edge and a second barrier lateral edge,
wherein the absorbent core comprises absorbent material enclosed in a core wrap, the core wrap having a maximum length, $L_{CW}$, and wherein $L_{CW}$ is substantially the same as $L_{BS}$,
wherein the absorbent core comprises a pair of permanent channels substantially free of the absorbent material, and
wherein the outer cover forms an outer wrap configured to wrap the first waist region, the crotch region, and the second waist region.

2. The absorbent article of claim 1, comprising elastic members disposed on the outer wrap.

3. The absorbent article of claim 1, wherein the chassis comprises a first barrier leg cuff extending at least partially between a first lateral chassis edge and a second lateral chassis edge, on opposite sides of the longitudinal centerline and being at least present in the crotch region.

4. The absorbent article of claim 3, wherein the chassis comprises a second of barrier leg cuff extending at least partially between the first lateral chassis edge and the second lateral chassis edge, and wherein the first barrier leg cuff and the second barrier leg cuff extend on opposite sides of the longitudinal centerline.

5. The absorbent article of claim 4, wherein each of the first and second barrier leg cuffs comprise proximal edges directly joined to the backsheet.

6. The absorbent article of claim 1, wherein the waist feature comprises a nonwoven web of fibers, wherein the fibers are at least one of spunbond, spunlaid, meltblown, spunmelt, solvent-spun, electrospun, carded, film fibrillated, melt-film, fibrillated, air-laid, dry-laid and wet-laid staple fibers.

7. The absorbent article of claim 6, wherein the fibers comprise bi-component fibers.

8. The absorbent article of claim 1, comprising a refastenable side seams.

9. The absorbent article of claim 1, comprising an absorbent material deposition area comprising the absorbent material, wherein the absorbent material deposition area having a maximum length, $L_{AB}$, extending between a first absorbent area lateral edge and a second absorbent area lateral edge, wherein $L_{AB}$ is about 90% or greater of $L_{BS}$.

10. The absorbent article of claim 1, wherein the free portion of waist feature extends longitudinally outboard of the chassis by a minimum distance E, wherein E is about 15 mm or greater.

11. The absorbent article of claim 1, wherein the waist feature comprises a pocket formed from a portion of the waist feature that is at least partially unattached from the chassis.

12. The absorbent article of claim 1, comprising a fastening system.

13. The absorbent article of claim 1, wherein the absorbent article comprises a pant.

14. The absorbent article of claim 1, comprising a maximum length, L, and wherein the maximum length of the barrier layer, $L_{BS}$, is less than about 75% of L.

15. An absorbent article comprising:
a first waist region, a second waist region, and a crotch region disposed between the first and second waist regions; a longitudinal centerline and a lateral centerline;
a chassis comprising a topsheet, a backsheet and an absorbent core disposed between the topsheet and the backsheet; and
a waist feature joined to the chassis in at least one of the first waist region and the second waist region, wherein the waist feature comprises a free portion extending longitudinally outboard of the chassis and laterally outboard of the chassis in at least one of the first waist region and the second waist region such that the free portion does not overlap the chassis,
wherein the backsheet comprises a barrier layer having a maximum length, $L_{BS}$, extending between a first barrier lateral edge and a second barrier lateral edge;
wherein the absorbent core comprises absorbent material enclosed in a core wrap, the core wrap having a maximum length, $L_{CW}$, and wherein $L_{CW}$ is substantially the same as $L_{BS}$,
wherein the absorbent core comprises a pair of permanent channels substantially free of the absorbent material, and
wherein portions of the waist feature at least partially wrap about the absorbent core.

16. The absorbent article of claim 15, wherein the absorbent material is disposed in an absorbent material deposition area, the absorbent material deposition area having a maximum length, $L_{AB}$, extending between a first absorbent area lateral edge and a second absorbent area lateral edge, wherein $L_{AB}$ is about 90% or greater of $L_{BS}$.

17. The absorbent article of claim 15, wherein the free portion of waist feature extends longitudinally outboard of the chassis by a minimum distance E, and where E is about 15 mm or greater.

18. An absorbent article comprising:
a first waist region, a second waist region, and a crotch region disposed between the first and second waist regions; a longitudinal centerline and a lateral centerline;
a chassis comprising a topsheet, a backsheet and an absorbent core disposed between the topsheet and the backsheet; and
a waist feature joined to the chassis in at least one of the first waist region and the second waist region, wherein the waist feature comprising a free portion extending longitudinally outboard of the chassis in at least one of the first waist region and the second waist region such that the free portion does not overlap the chassis,
wherein the backsheet comprises a barrier layer having a maximum length, $L_{BS}$, extending between a first barrier lateral edge and a second barrier lateral edge;
wherein the absorbent core comprises absorbent material enclosed in a core wrap, the core wrap having a maximum length, $L_{CW}$,
wherein the absorbent material is disposed in an absorbent material deposition area, the absorbent material deposition area having a maximum length, $L_{AB}$, extending between a first absorbent area lateral edge and a second absorbent area lateral edge, wherein $L_{AB}$ is about 90% or greater of $L_{BS}$,
wherein the first absorbent area lateral edge is disposed a longitudinal distance, D1, from the first barrier lateral edge, wherein D1 is 5% or less of $L_{BS}$, and
wherein the absorbent core comprises a pair of permanent channels substantially free of absorbent material.

19. The absorbent article of claim 18, wherein $L_{CW}$ is substantially the same as $L_{BS}$.

20. The absorbent article of claim 18, comprising a total absorbent capacity at least about 200 g according to the CRC test method herein.

* * * * *